United States Patent
Selkee

(10) Patent No.: US 8,021,327 B2
(45) Date of Patent: *Sep. 20, 2011

(54) STEERING MECHANISM FOR BI-DIRECTIONAL CATHETER

(75) Inventor: Thomas V. Selkee, Claremont, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 12/355,667

(22) Filed: Jan. 16, 2009

(65) Prior Publication Data

US 2009/0182269 A1 Jul. 16, 2009

Related U.S. Application Data

(63) Continuation of application No. 10/871,682, filed on Jun. 14, 2004, now Pat. No. 7,591,799.

(51) Int. Cl.
*A61M 37/00* (2006.01)
(52) U.S. Cl. .................................. 604/95.04; 604/528
(58) Field of Classification Search ............... 604/95.01, 604/95.04, 528, 585
See application file for complete search history.

(56) References Cited

U.S. PATENT DOCUMENTS

| | | | |
|---|---|---|---|
| 5,273,535 A | 12/1993 | Edwards et al. | |
| RE34,502 E | 1/1994 | Webster, Jr. | |
| 5,358,478 A | 10/1994 | Thompson et al. | |
| 5,395,327 A | 3/1995 | Lundquist et al. | |
| 5,395,328 A | 3/1995 | Ockuly et al. | |
| 5,456,664 A | 10/1995 | Heinzelman et al. | |
| 5,531,686 A | 7/1996 | Lundquist et al. | |
| 5,562,619 A | 10/1996 | Mirarchi et al. | |
| 5,571,085 A | 11/1996 | Accisano, III | |
| 5,626,553 A | 5/1997 | Frassica et al. | |
| 5,676,653 A | 10/1997 | Taylor et al. | |
| 5,741,320 A | 4/1998 | Thornton et al. | |
| 5,891,088 A | 4/1999 | Thompson et al. | |
| 5,944,690 A | 8/1999 | Falwell et al. | |
| 6,033,378 A | 3/2000 | Lundquist et al. | |
| 6,171,277 B1 | 1/2001 | Ponzi | |
| 6,198,974 B1 | 3/2001 | Webster, Jr. | |

(Continued)

OTHER PUBLICATIONS

European Search Report dated Oct. 18, 2005 from European Patent Application No. EP05253625.7.

*Primary Examiner* — Nicholas D Lucchesi
*Assistant Examiner* — Laura A Bouchelle
(74) *Attorney, Agent, or Firm* — Christie, Parker & Hale, LLP

(57) ABSTRACT

A bi-directional catheter with nearly double the throw in its catheter tip deflection defines a puller wire travel path having a U-turn a pulley which minimizes the offset angle between the puller wire and the longitudinal axis of the control handle while maximizing the travel distance of that puller wire for any given distance traveled by the pulley drawing the puller wire. In particular, the control handle of the catheter which includes a steering assembly having a lever arm carrying a pair of pulleys for drawing corresponding puller wires to deflect the tip section of the catheter. The pulleys are rotatably mounted on opposing portions of the lever arm such that one pulley is moved distally as the other pulley is moved proximally when the lever arm is rotated. Because each puller wire is trained on a respective pulley, rotation of the lever arm causes the pulley that is moved proximally to draw its puller wire to deflect the tip section in the direction of the off-axis lumen in which that puller wire extends.

24 Claims, 9 Drawing Sheets

U.S. PATENT DOCUMENTS

| | | |
|---|---|---|
| 6,210,407 B1 | 4/2001 | Webster |
| 6,485,455 B1 | 11/2002 | Thompson et al. |
| 6,530,897 B2 | 3/2003 | Nardeo |
| 6,579,278 B1 | 6/2003 | Bencini |
| 6,599,265 B2 | 7/2003 | Bon |
| 6,648,875 B2 | 11/2003 | Simpson et al. |
| 6,652,506 B2 | 11/2003 | Bowe et al. |
| 2002/0177766 A1 | 11/2002 | Mogul |

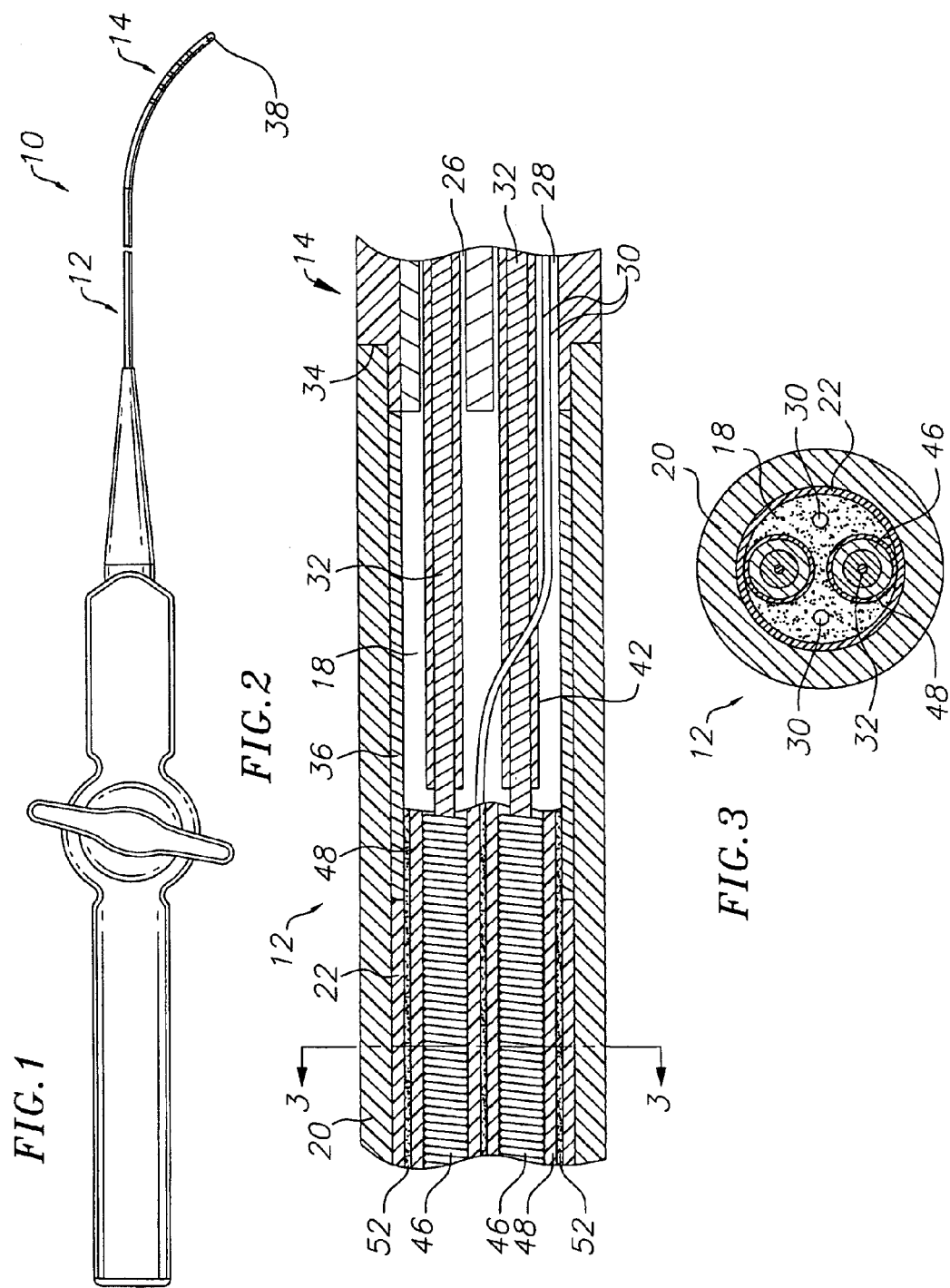

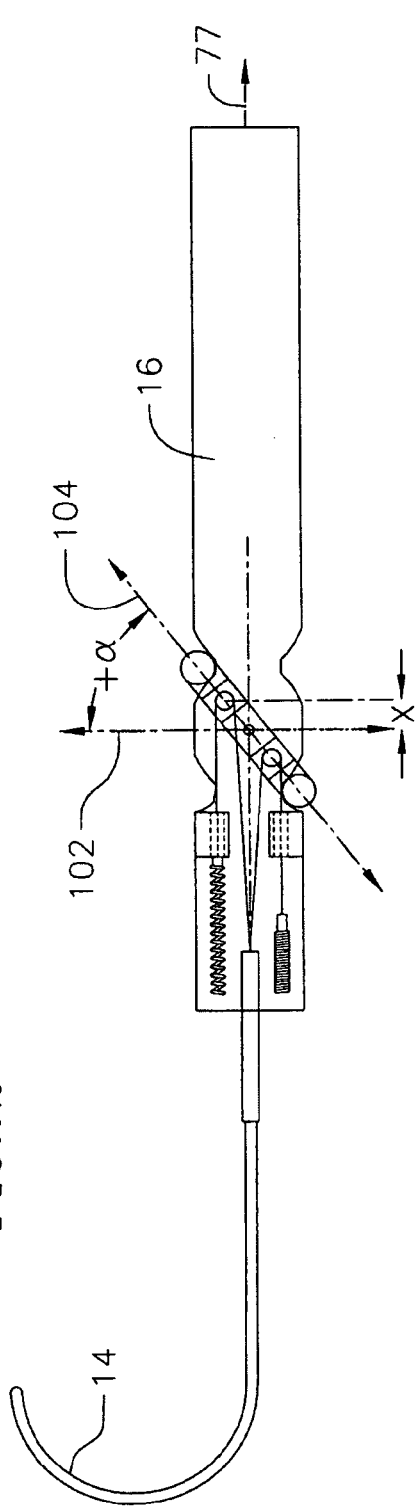

STEERING MECHANISM FOR BI-DIRECTIONAL CATHETER

CROSS-REFERENCE TO RELATED APPLICATION(S)

This application is a continuation of U.S. patent application Ser. No. 10/871,682 filed Jun. 14, 2004 now U.S. Pat. No. 7,591,799, and entitled STEERING MECHANISM FOR BI-DIRECTIONAL CATHETER, the entire content of which is incorporated herein by reference.

FIELD OF INVENTION

The present invention relates to improved bidirectional steerable catheters, and more particularly to catheters having bidirectional control handles.

BACKGROUND OF INVENTION

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Bidirectional catheters have been designed to be deflectable in one direction by one puller wire and in the opposite direction within the same plane by a second puller wire. In such a construction, the puller wires extend into opposing off-axis lumens within the tip section of the catheter. So that the tip section can bend in both directions in the same plane, the puller wires and their associated lumens must be located along a diameter of the tip section. For ablation catheters, electrode lead wires must also be provided within the distal end. Typically, an additional lumen is used to contain the electrode lead wires. For example, U.S. Pat. No. 6,210,407, the disclosure of which is incorporated herein by reference, is directed to a bi-directional catheter comprising two puller wires and a control handle having at least two moveable members longitudinally movable between first and second positions. The proximal end of each puller wire is connected to an associated movable member of the control handle. Proximal movement of a movable member relative to the catheter body results in proximal movement of the puller wire associated with that movable member relative to the catheter body, and thus deflection of the tip section in the direction of the lumen in which that puller wire extends As another example, U.S. Pat. No. 6,171,277, the disclosure of which is incorporated herein by reference, is directed to a bidirectional steerable catheter having a control handle that houses a generally-circular spur gear and a pair of spaced apart rack gears. Each rack gear is longitudinally movable between first and second positions, whereby proximal movement of one rack gear results in rotational movement of the spur gear, and correspondingly distal movement of the other rack gear. Two puller wires extend from the control handle whose the distal ends are fixedly attached to the tip section, and whose proximal ends are each anchored to a separate associated rack gear in the control handle. Proximal movement of a rack gear and its associated puller wire relative to the catheter body results in deflection of the tip section in the direction of the off axis lumen into which that puller wire extends.

Also known is U.S. Pat. No. 6,198,974, the disclosure of which is incorporated herein reference, is directed to a bi-directional electrode catheter comprising a control handle. At their proximal ends, two pairs of puller wires are attached to movable pistons in the control handle. Each piston is controlled by an operator using a slidable button fixedly attached to each piston. Movement of selected buttons results in deflection of the tip section into a generally planar "U"- or "S"-shaped curve.

Further known is U.S. Pat. No. 5,891,088, the disclosure of which is incorporated, directed to a steering assembly with asymmetric left and right curve configurations. Proximal ends of left and right steering wires are adjustably attached to a rotatable cam housed in a control handle. The rotatable cam has first and second cam surfaces which may be configured differently from each other to accomplish asymmetric steering.

While the aforementioned catheters provide bi-directional steering, the mechanical efficiencies of the steering or deflection mechanism can be improved upon. Because the control handle has limited interior space in which to house the steering mechanism, a need exists for a compact yet mechanically-efficient design to accomplish bi-directional steering. Moreover, a greater degree of deflection in the catheter tip is also desirable, particularly if it can be accomplished without requiring greater exertion on the part of the user. The steering assembly of aforementioned U.S. Pat. No. 5,891,088 employs a configuration whereby the puller wires extend to the cam surfaces of the rotatable cam at a greater than generally desirable angle from the longitudinal axis of the catheter shaft, which decreases the efficiency of the steering lever and adds to friction losses in the operation of the steering assembly. In addition, the steering assembly therein generally limits the amount of longitudinal movement of the puller wires for deflecting the catheter tip to only the circumference of the rotatable cam. An improved catheter with bi-directional deflection is therefore desired.

SUMMARY OF THE INVENTION

The present invention provides a bi-directional catheter with nearly double the throw in its catheter tip deflection. In particular, the travel path of each the puller wire includes a U-turn or doubling-back around a pulley which minimizes the offset angle between the puller wire and the longitudinal axis of the control handle while maximizing the travel distance of that puller wire for any given distance traveled by the pulley drawing the puller wire.

In one embodiment, the catheter has an elongated catheter body, a catheter tip section with first and second diametrically-opposed off-axis lumens, and a control handle which includes a steering assembly having a lever arm carrying a pair of pulleys for drawing corresponding puller wires to deflect the tip section of the catheter. The pulleys are rotatably mounted on opposing portions of the lever arm such that one pulley is moved distally as the other pulley is moved proximally when the lever arm is rotated. Because each puller wire is trained on a respective pulley, rotation of the lever arm causes the pulley that is moved proximally to draw its puller wire to deflect the tip section in the direction of the off-axis lumen in which that puller wire extends.

In a detailed embodiment of the invention, each puller wire is trained about its respective pulley for at least about 180 degrees. Moreover, each puller wire may extend from the distal end of the control handle to its respective pulley at a predetermined angle generally less than 10 degrees from the longitudinal axis of the control handle. Furthermore, the range of rotation of the lever arm deflecting the catheter tip can be predetermined through a predetermined profile or curvature in the housing of the control handle.

In another embodiment of the invention, the catheter includes a pair of constant force springs that draw up slack in a puller wire when the tip is deflected. The catheter may also include a pair of adjustable stops that are configured to prevent proximal movement of each proximal end of the puller wires beyond a respective predetermined stop location in the control handle. Coarse and fine adjustments in each stop location are accomplished through adjustable positioning and configuration of the stops within the catheter housing.

In yet another embodiment, the catheter includes a deflection knob that is rotationally coupled to the lever arm which enables the user to control deflection of the tip section with, preferably, a thumb and an index finger, when grasping the control handle. The catheter may also include a tension adjustment mechanism for adjusting the tightness of the deflection knob.

BRIEF DESCRIPTION OF THE DRAWINGS

These and other features and advantages of the present invention will be better understood by reference to the following detailed description when considered in conjunction with the accompanying drawings wherein:

FIG. 1 is a side view of an embodiment of the catheter of the invention.

FIG. 2 is a side cross-sectional view of the junction of the catheter body and tip section of an embodiment of a catheter according to the invention.

FIG. 3 is a transverse cross-sectional view of the catheter body shown in FIG. 2 taken along line 3-3.

FIG. 12 shows components of the steering assembly for deflection of the tip section to the right.

FIG. 13 shows components of the steering assembly for deflection of the tip section to the left.

DETAILED DESCRIPTION OF THE INVENTION

Figure 4:
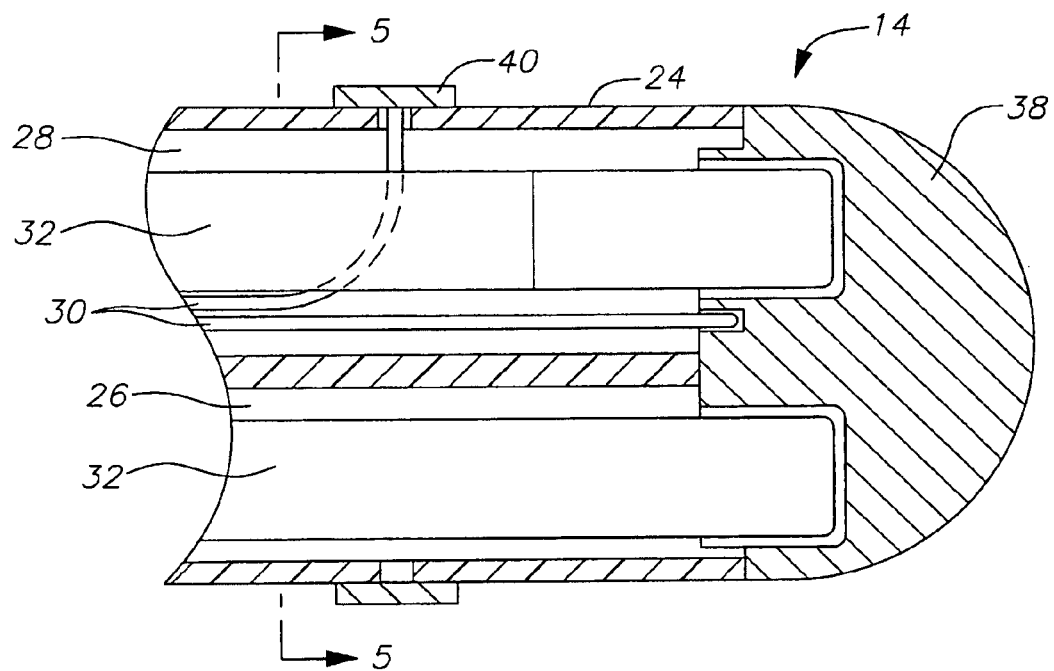
FIG. 4 is a side cross-sectional view of the distal end of the tip section shown in FIG. 2.

In an embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch.

Figure 5:
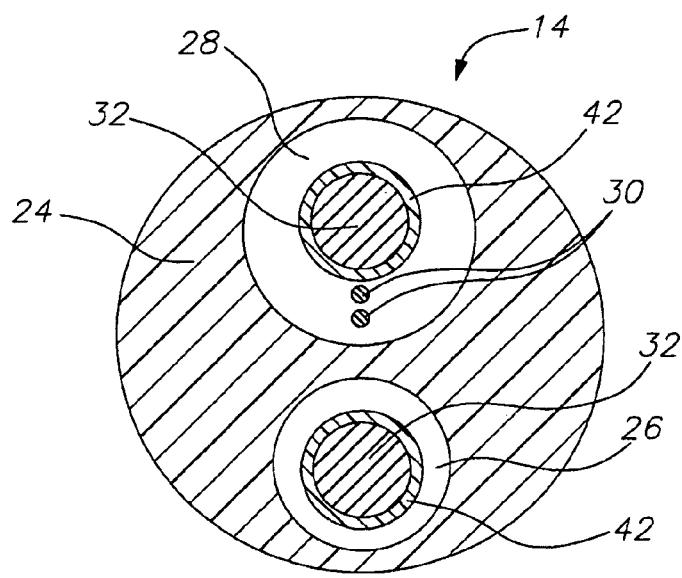
FIG. 5 is a transverse cross-sectional view of the tip section along line 5-5.
Figure 6:
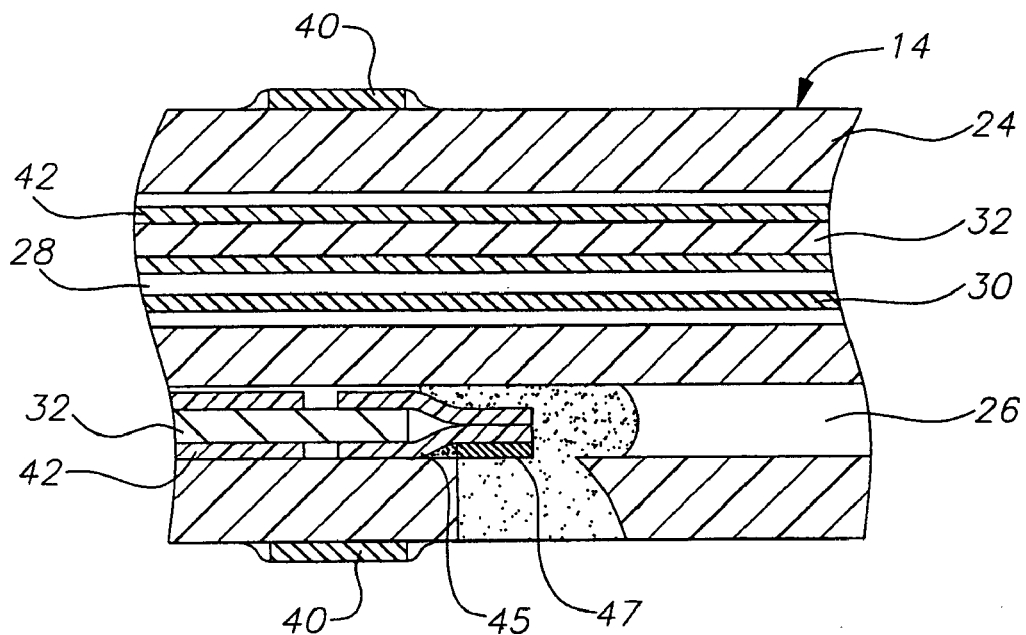
FIG. 6 is a transverse cross-sectional view of a catheter tip section according to the invention where the puller wires are anchored to the side walls of the tip section.

As shown in FIGS. 4 and 5, the tip section 14 comprises a short section of flexible tubing 24 having a first off-axis lumen 26 and a second off-axis lumen 28. The flexible tubing 24 is made of a suitable non-toxic material that is preferably more flexible than the catheter body 20. A presently preferred material for the tubing 24 is braided polyurethane, i.e., polyurethane with an embedded mesh of braided stainless steel or the like. The outer diameter of the tip section 14, like that of the catheter body 12, is preferably no greater than about 7 french, more preferably about 6½ french or less.

The off-axis lumens 26, 28 extend through diametrically opposed halves of the tip section 14. The off-axis lumens 26, 28 are asymmetrical and therefore non-interchangeable. The first off-axis lumen 26 is smaller than the second off-axis lumen 28. In an 8 french or 7 french diameter catheter, where the tip section is 6½ french, it is preferred that the first off-axis lumen 26 has a diameter ranging from about 0.018 inch to about 0.025 inch, more preferably from about 0.018 inch to about 0.022 inch. Preferably, the second off-axis lumen 28 has a diameter ranging from about 0.022 inch to about 0.030 inch, more preferably from about 0.026 inch to about 0.028 inch.

By using two rather than three lumens along a single diameter, the present design retains the simplified construction of the unidirectional deflectable steerable catheter described in U.S. Pat. No. Re 34,502, which is incorporated herein by reference. However, it is understood that additional lumens may be provided in the tip section. As described in U.S. Pat. No. 6,171,277, the disclosure of which is incorporated herein by reference, the tip section 14 may contain four lumens, two of which have a greater diameter of about 0.029 inch and two of which have a lesser diameter of about 0.018 inch. Lead wires for the electrodes, thermocouple wires and/or electromagnetic sensor cable may extend through different lumen(s)

from those through which each of puller wires extends. As such, the present invention may employ two or more lumens in the tip section 14.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast drying glue, e.g. Super Glue®. Thereafter a second glue joint is formed between the proximal ends of the stiffening tube 22 and outer wall 20 using a slower drying but stronger glue, e.g., polyurethane.

A spacer 36 lies within the catheter body 12 between the distal end of the stiffening tube 22 and the proximal end of the tip section 14. The spacer 36 is preferably made of a material that is stiffer than the material of the tip section 14, e.g., polyurethane, but not as stiff as the material of the stiffening tube 22, e.g. polyimide. A spacer made of Teflon® is presently preferred. A preferred spacer 36 has a length of from about 0.25 inch to about 0.75 inch, more preferably about 0.50 inch. Preferably the spacer 36 has an outer and inner diameter about the same as the outer and inner diameters of the stiffening tube 22. The spacer 36 provides a transition in flexibility at the junction of the catheter body 12 and the tip section 14 to bend smoothly without folding or kinking.

In the depicted embodiment, the distal end of the tip section 14 carries a tip electrode 38 (see FIGS. 1 and 4). Mounted along the length of the tip section 14 is a ring electrode 40 (see FIG. 4). The length of the ring electrode 40 is not critical, but is preferably about 1 mm to about 3 mm.

Additional ring electrodes can be provided if desired. If multiple ring electrodes are used, they are spaced apart in any fashion as desired so long as their edges do not touch.

As shown in FIGS. 2-5, the tip electrode 38 and ring electrode 40 are each connected to a separate lead wire 30. Each lead wire 30 extends through the second off-axis lumen 28 in the tip section 14 (FIG. 5), through the central lumen 18 in the catheter body 12 (FIG. 3) and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like. Connection of a lead wire 30 to the ring electrode 40 is preferably accomplished by first making a small hole through the tubing 24. Such a hole can be created, for example, by inserting a needle through the tubing 24 and heating the needle sufficiently to form a permanent hole. The lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like.

As also shown in FIGS. 2-5, two puller wires 32 extend through the catheter 10. Each puller wire 32 extends from the control handle 16, through the central lumen 18 in the catheter body 12 (FIG. 3) and into one of the off-axis lumens 26 and 28 of the tip section 14 (FIG. 5). As described in more detail below, the proximal end of each puller wire 32 is anchored within the control handle 16 and the distal end of each puller wire 32 is anchored within the tip section Each puller wire 32 is made of any suitable metal, such as stainless steel or Nitinol. Preferably each puller wire 32 has a coating, such as a coating of Teflon® or the like. Each puller wire 32 has a diameter preferably ranging from about 0.006 inch to about 0.0010 inch. Preferably both of the puller wires 32 have the same diameter.

Each puller wire 32 is anchored near the distal end of the tip section 14. In the embodiment depicted in FIG. 4, the puller wires 32 are both anchored to the tip electrode 38 by a welding or the like.

Figures 7, 8:
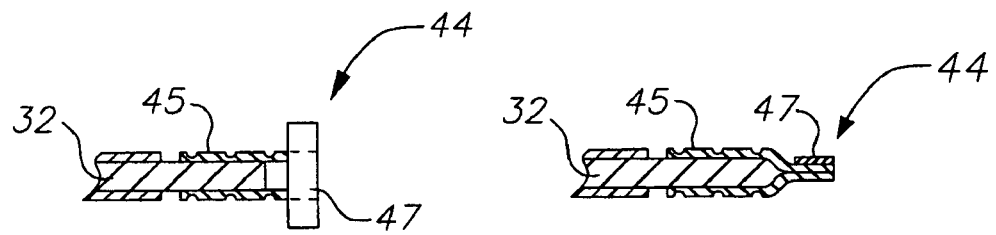
FIG. 7 is a longitudinal cross-sectional view of a preferred puller wire T-bar anchor.
FIG. 8 is a longitudinal cross-sectional view of the puller wire T-bar anchor of FIG. 7 rotated 90.degree. to show the cross-piece on end.
Figure 9:
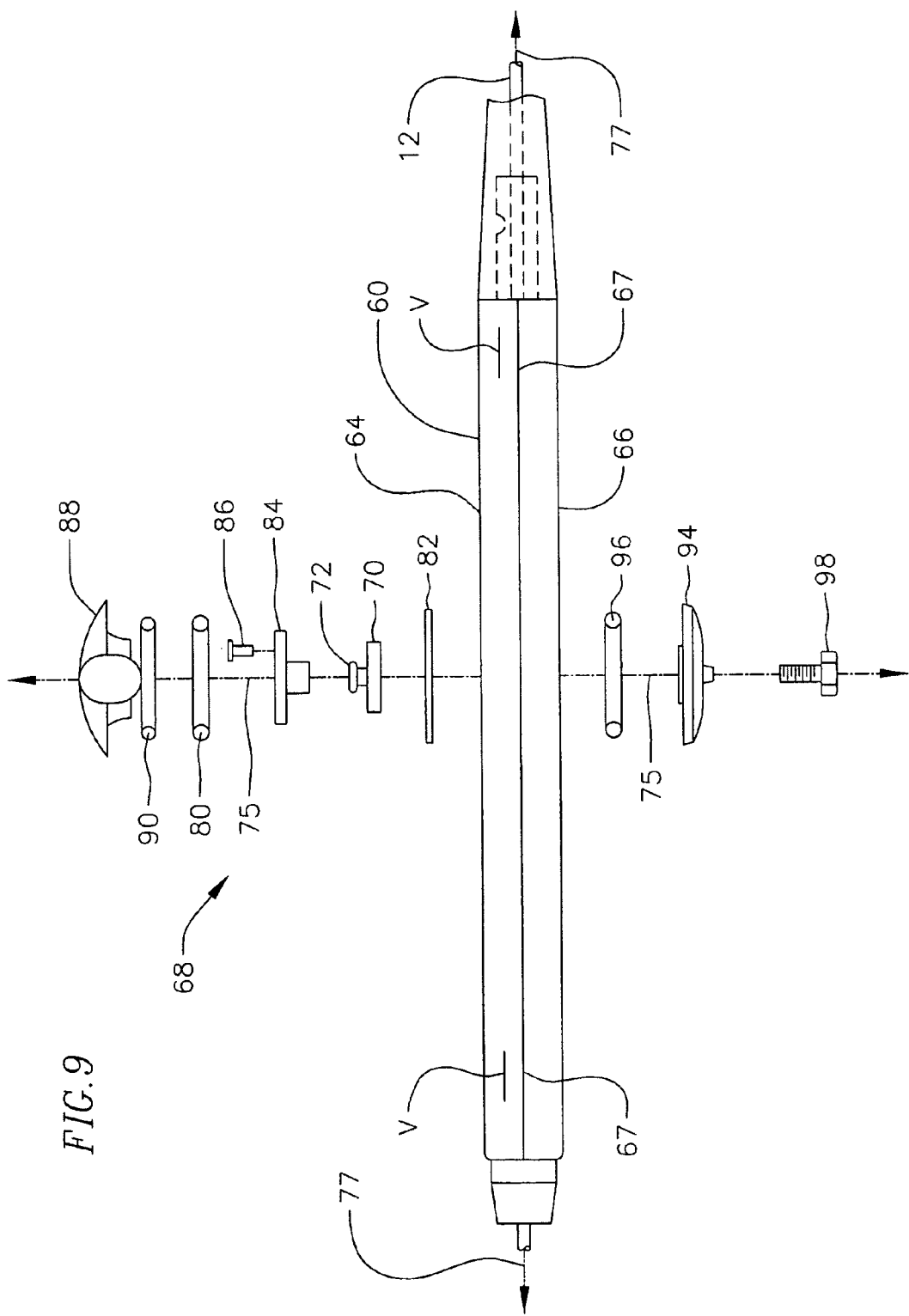
FIG. 9 is a top exploded view of a control handle of the catheter of FIG. 1.

Alternatively, the puller wire 32 in the first off-axis lumen 26 can be anchored to the side wall of the tip section 14. As shown in FIGS. 7 to 9, the puller wire 32 is preferably attached by means of an anchor 44 fixedly attached to the distal end of the puller wire 32. The anchor 44 is formed by a metal tube 45, e.g., a short segment of hypodermic stock, that is fixedly attached, e.g. by crimping, to the distal end of the puller wire 32. The tube has a section that extends a short distance beyond the distal end of the puller wire 32. A cross-piece 47 made of a small section of stainless steel ribbon or the like is soldered or welded in a transverse arrangement to the distal end of the metal tube which is flattened during the operation. This creates a T-bar anchor 44. A notch is created in the side of the tip section 14 resulting in an opening in the off-axis lumen 26 carrying the puller wire 32. The cross piece 47 lies transversely within the notch. Because the length of the ribbon forming the cross-piece 47 is longer than the diameter of the opening into the off-axis lumen 26, the anchor 44 cannot be pulled completely into the off-axis lumen 26. The notch is then sealed with polyurethane glue or the like to give a smooth outer surface. The glue flows into the off-axis lumen 26 to fully secure the anchor. A tunnel, in the form of polyimide tubing or the like, can be provided to permit passage of the lead wire 30 through the glue so that this same puller wire anchor construction can be used in the second off-axis lumen 28. Other means for anchoring the puller wires 32 in the tip section 14 would be recognized by those skilled in the art and are included within the scope of the invention.

Referring back to FIGS. 1 and 2, the catheter 10 further comprises two compression coils 46, each in surrounding relation to a corresponding puller wire 32. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. The non-conductive sheath 48 made of thin-walled polyimide tubing is presently preferred.

As shown in FIG. 2, at the distal end of the catheter body, the two compression coils 46 are positioned in diametric opposition within the stiffening tube 22 and spacer 36 so that they can be aligned with the two off-axis lumens 26, 28 in the tip section 14. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

Still referring to FIG. 2, the distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 26, 28 of the tip section 14 and are anchored at their distal ends to the proximal end of the tip section 14 by a glue joint. In the depicted embodiment, where the compression coils 46 are each surrounded by the sheath 48, care should be taken to insure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

Both glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 18 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care must be taken to insure that glue does not wick over the end of the coil so that the puller wire cannot slide within the coil.

As best shown in FIGS. 2 and 5, within the off-axis lumens 26, 28, each puller wire 32 is surrounded by a plastic sheath 42, preferably made of Teflon®. The plastic sheaths 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Longitudinal movement of the puller wires 32 relative to the catheter body 12, which results in deflection of the tip section 14, is accomplished by manipulation of the control handle 16. A suitable bidirectional control handle for use in the present invention is illustrated in FIGS. 9-15.

As shown in FIG. 9, the control handle 16 comprises a generally elongated handle housing 60, which can be made of any suitable rigid material. The housing 60 can be of a unitary construction or of two opposing halves 64, 66 that are joined by glue, sonic welding or other suitable means along a longitudinal peripheral seam 67. The control handle 16 comprises a steering assembly 68 that controls deflection of the tip section in response to manipulations by the user. In the illustrated embodiment, the steering assembly comprises a lever arm 70 carrying a pair of coordinated pulleys 72 that act on the puller wires 32 to deflect the tip section. The lever arm 70 of the steering assembly 68 is seated for rotation between a top washer 80 and a bottom washer 82. A friction nut 84 and a pin 86 couple an external deflection knob 88 to the lever arm. The deflection knob seats against an O-ring 90. Movement of the deflection knob 88 by the user rotates the lever arm 70 about a screw 98 within the housing 60, as explained below in further detail. Contact between deflection knob 88 and the side of the housing 60 physically limits the range of left and right rotation of the lever arm about a throw axis 75.

The steering assembly 68 also includes an external tension adjustment knob 94 that an adhesive couples to the head of the screw 98. The tension adjustment knob 94 seats against another O-ring 96. Movement of the knob 94 rotates the screw 98. Clockwise rotation of the knob 94 tightens the screw 98 to increase the seating force between the lever arm and the bottom washer 82. When moved fully clockwise to contact against the housing, the knob 94 imposes a seating force that prevents rotation of the lever arm 70 by the deflection knob 88. Counterclockwise movement of the tension adjustment knob 94 loosens the screw 98 to decrease the seating force and free the lever arm 70 for rotation.

Figure 10:
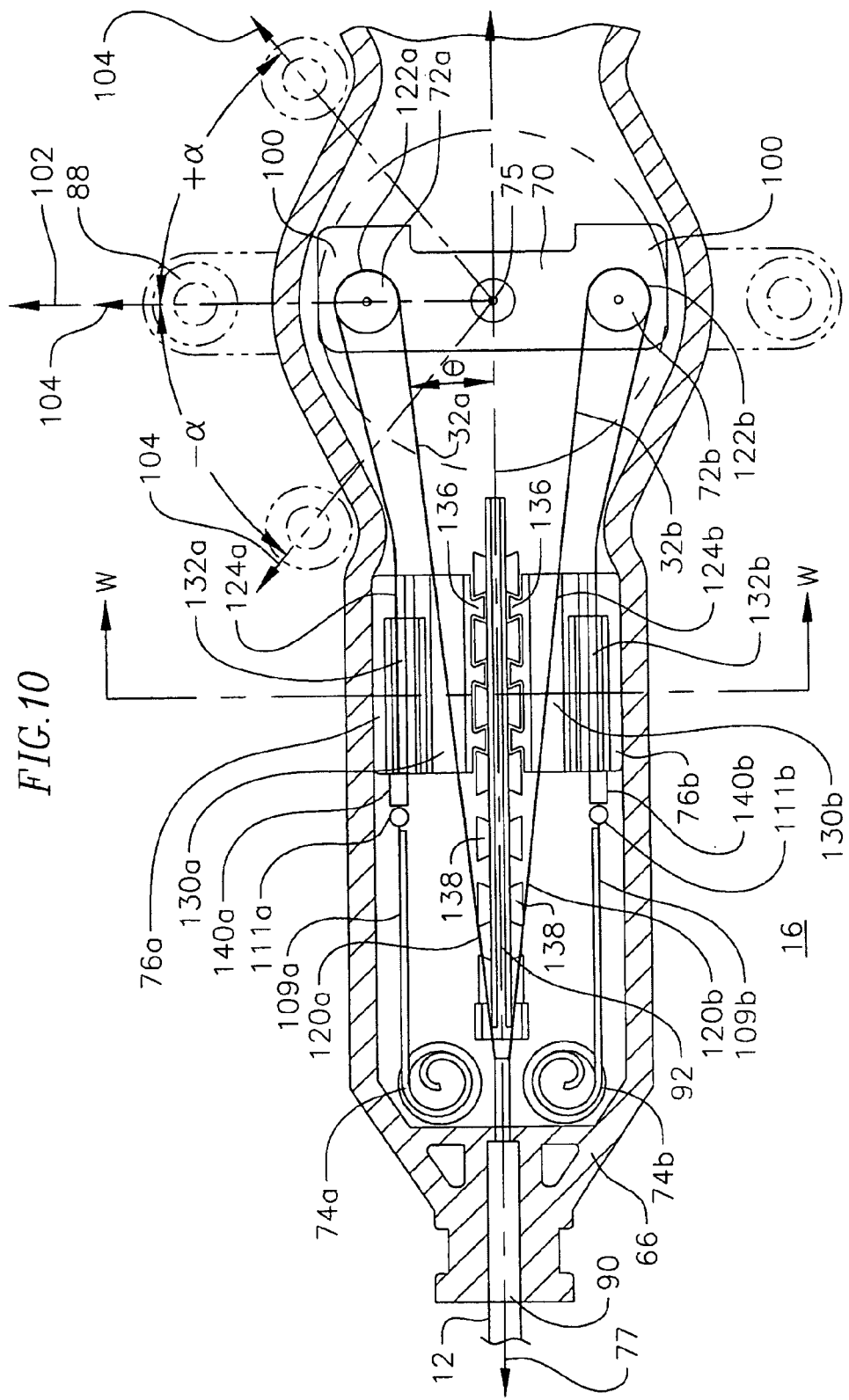
FIG. 10 is a view of a control handle of the catheter of FIG. 9 taken generally along Line V-V with parts broken away for clarity.

As shown in FIG. 10, the lever arm 70 has a rotation angle about a throw axis 75, which is generally perpendicular to a longitudinal axis 77 of the control handle 16. A neutral position along axis 102 is defined for the lever arm when its longitudinal axis 104 is generally perpendicular to the longitudinal axis 77 of the control handle 16. The lever arm is rotatable from its neutral position in the clockwise direction by angle $+\alpha$ and in the counterclockwise direction by angle $-\alpha$. Because the lever arm is rotationally coupled to the deflection knob 88, the range of the angle $\alpha$ is also limited by the contact of the deflection knob 88 with the housing 60. In the disclosed embodiment, the angle $\alpha$ ranges between about 0 and 70 degrees, preferably between about 30 and 60 degrees and more preferably between about 40 to 50 degrees. Accordingly, the disclosed embodiment provides a total range of rotation (from $-\beta$ to $+\alpha$) of between about 0 and 140 degrees, preferably between about 60 and 120 degrees and more preferably between about 80 to 100 degrees.

Figure 11:
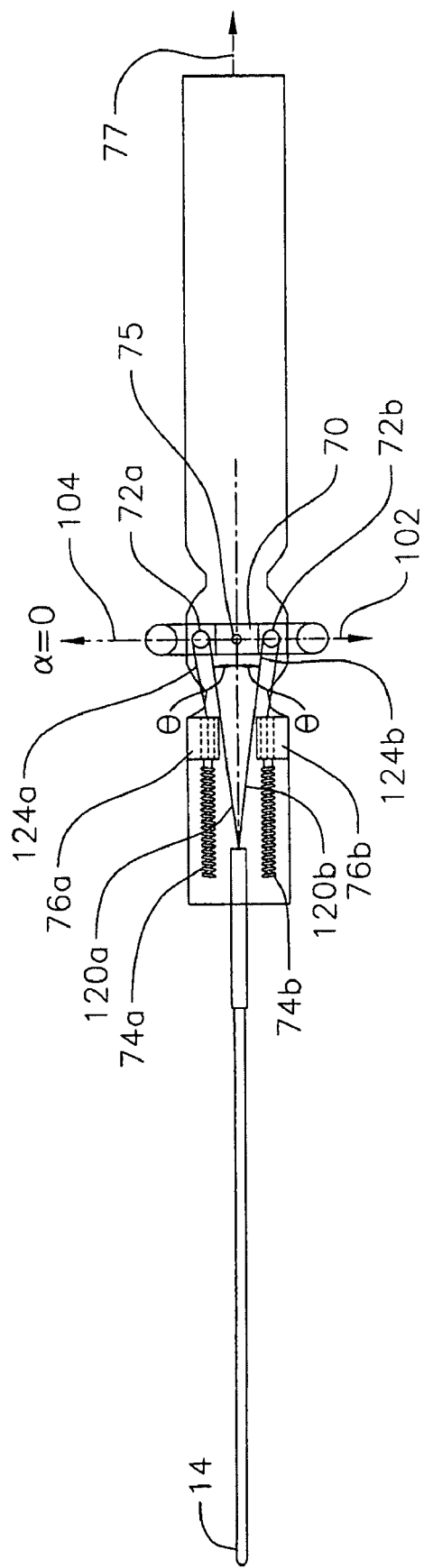
FIG. 11 shows components of the steering assembly without deflection in the tip section of the catheter.

The pulleys 72 are located at opposing ends of the lever arm 70, at a radial distance R from the throw axis 75. As shown in FIGS. 11-13, with rotation of the lever arm 70, one pulley 72 is translated distally as the other pulley 72 is translated proximally. Moreover, each pulley can rotate counterclockwise or clockwise about its own axis of rotation.

In accordance with the present invention, the steering assembly 68 is advantageously configured to provide a relatively shorter angular throw while increasing, if not at least generally doubling, the throw capacity of the catheter. In particular, the steering assembly has a minimized moment of inertia about the throw axis 75, while generally doubling the travel distance of a puller wire in relation to the travel distance of the respective pulley drawing that puller wire, despite the relatively small interior of the housing. Moreover, the steering assembly provides a minimal angle between the longitudinal axis 77 of the control handle 16 and a segment of the puller wire drawn to accomplish deflection, for more efficient use of the force applied by the user in operating the control handle. To facilitate these movements for deflecting the tip section, the steering assembly 68 also includes a pair of constant force springs 74 that are attached to the proximal ends of the puller wires, and a pair of adjustable stops 76 which prevent the proximal ends of the puller wires from moving proximally past a selected position relative to the longitudinal axis of the control handle.

Referring back to FIG. 10, the housing 60 is configured at its distal end with a port 90 through which proximal end segments of the puller wires 32 enter the control handle 16. In the housing half 66, a divider 92 is configured in the inner surface and distal of the port to extend linearly between the port and the lever arm 70. At a distal end 94 of the divider, the puller wires (now designated as 32a, 32b) diverge toward a respective pulley 72 in the lever arm. For ease of discussion, the housing half 66 may be described as divisible along the divider 92 into top and bottom housing quarters 96a, 96b, which are more or less mirror counterparts of each other in terms of physical layout and operation. Accordingly, the following description uses similar reference numerals for similar structures except the numerals are followed by the letter a or the letter b.

Figure 15:
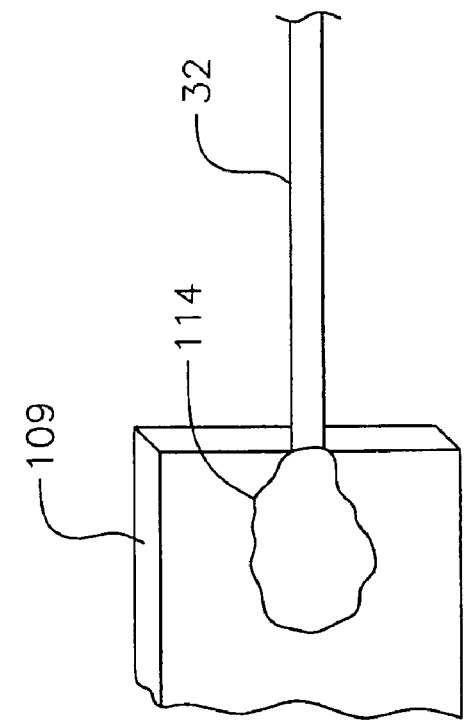
FIG. 15 is a side view of a free end of a spring fastened to a proximal end of a puller by a welded joint.
Figure 14:
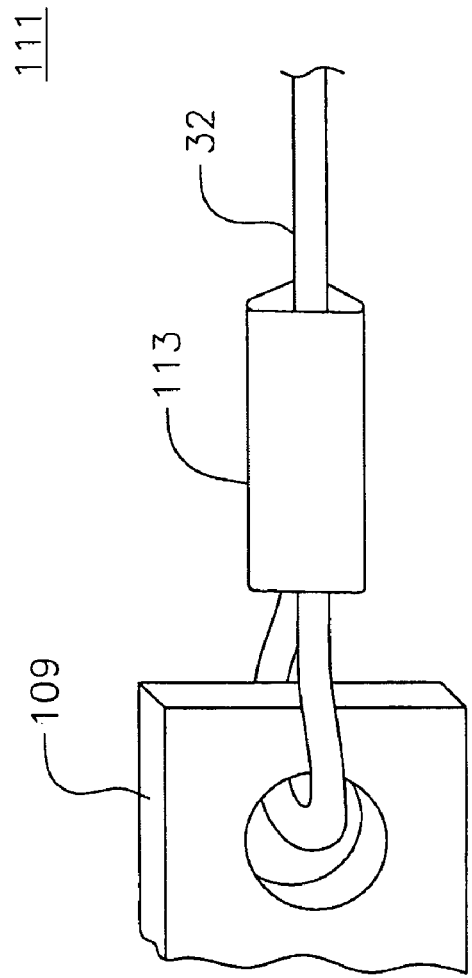
FIG. 14 is a side view of a free end of a spring fastened to a proximal end of a puller wire by a crimp fastener.

The puller wire 32a continues from the port 90 proximally in a minimally diagonal and generally linear direction toward the pulley 72a in the lever arm 70. At the pulley 72a, the puller wire 32a is trained counterclockwise about the pulley before it extends distally toward the spring 74a where its proximal end (so designated despite its being physically distal of a preceding segment) is attached to a free end 109a of the spring 74a by a fastener 111a, such as a welded joint 113 (FIG. 14) or a crimp fastener 114 (FIG. 15).

Correspondingly, the puller wire 32b continues from the port proximally in a minimally diagonal and generally linear direction toward the pulley 76b in the lever arm 70. At the pulley, the puller wire 32b is trained clockwise about the pulley before it extends distally toward the spring 74b where its proximal end, (so designated despite its being physically distal of a preceding segment) is attached to a free end 109b of the spring 74b by a fastener 111b, such as the welded joint 113 or the crimp fastener 114.

In the embodiment of FIG. 10, each puller wire is trained about its pulley for a predetermined degree ranging between about 185 to 215, preferably 190-210, or more preferably about 195-205. Moreover, in FIG. 10, the springs 76a, 76b are illustrated as flat coil springs. In general, each spring member exerts a force in the distal direction ranging between about 0.25 lbs. and 1.0 lbs, preferably ranging between about 0.4 lbs and 0.8 lbs, and preferably of about 0.6 lbs.

Figure 10A:
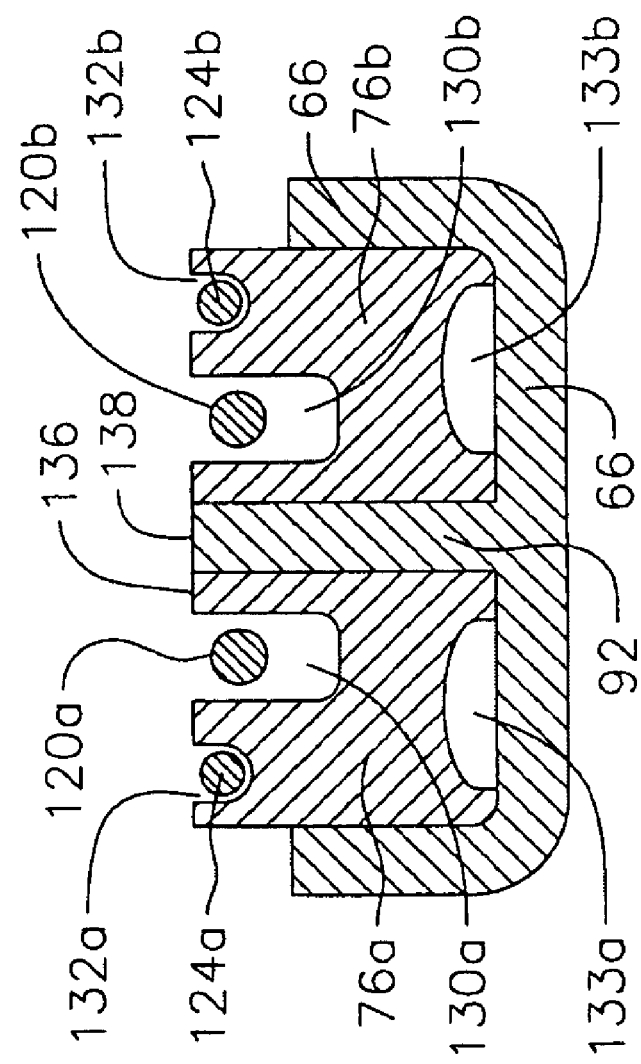
FIG. 10a is a view of the control handle of FIG. 10 taken generally along Line W-W.

In view of the foregoing, the travel path within the housing of each puller wire is as follows: a first generally linear path traversed by puller wire segments 120a, 120b between the port 90 and the respective pulley 72a, 72b, a non-linear (including, e.g., a U-turn or doubling back) path traversed by puller wire segments 122a, 122b generally around the respective pulley 72a, 72b, and a second generally linear path traversed by puller wire segments 124a, 124b between the respective pulley 72a, 72b and the respective springs 74a, 74b. In that regard, the stops 76a, 76b guide the direction of travel of the segments 120a, 120b and 124a, 124b. As best shown in FIG. 10a, each stop has a first channel 130 in which one of the segments 120a, 120b extends and a second channel 132 in which one of the segments 124a, 124b extends. While the first and second channels are sized to allow the wire segments to move distally or proximally, distal ends 135a, 135b of the second channels are configured to prevent proximal end 138a, 138b of the wires and/or the free ends 109a, 109b of the springs 74a, 74b from moving proximally past the distal ends 135a, 135b. Third channels 133a, 133b are provided so that other components of the catheter body (e.g., lead wires, irrigation tubes, etc.) can pass through the control handle without interfering with the steering assembly 68 and movements of the puller wire.

Given the foregoing, it can be seen from FIGS. 11-13 that rotation of the lever member 70 causes deflection in the catheter tip section 14. That is, when the lever member is rotated in the clockwise rotation (namely, in the +α direction) (FIG. 13b), the pulley 72a is translated proximally. Because the puller wire 32a trained on the pulley 72a is stopped at its proximal end by the stop 76a, the proximal translation of the pulley 72a causes it to rotate counterclockwise thereby drawing proximally the wire segment 120a, which results in deflection of the tip section 14 to the right.

Facilitating this deflection is the release of the segment 124b as the pulley 72b is coincidentally translated distally by the lever arm 70. The resulting slack in the segment 124b is taken up by the spring 74b (a tubular coil spring in the illustrated embodiment) as the pulley 72b rotates clockwise.

Correspondingly, when the lever arm is rotated in the counterclockwise rotation (namely, in the −α direction) (FIG. 13c), the pulley 72b is translated proximally. Because the puller wire 32b trained on the pulley 72b is stopped at its proximal end by the stop 76b, the proximal translation of the pulley 72b causes it to rotate clockwise thereby drawing proximally the wire segment 120b, which results in deflection of the tip section 14 to the left. Facilitating this deflection is the release of the segment 124a as the pulley 72a is coincidentally translated distally by the lever arm 70. The resulting slack in the segment 124a is taken up by the spring 74a (a tubular coil spring in the illustrated embodiment) as the pulley 72a rotates counterclockwise.

Although each of the actuating pulley has translated proximally only a distance x (FIGS. 12 and 13) along the longitudinal axis 77 as a result of the rotation of the lever arm 70, the length of the puller wire drawn by that pulley proximally from the port in deflecting the tip section is about 2x. Consequently, the present invention provides a catheter with nearly double the throw in tip deflection, despite the small interior space of the control handle.

Moreover, as also shown in FIGS. 11-13, an angle of alignment of the segments 120a, 120b deviates only minimally from the longitudinal axis 77 which provides greater operating efficiency in the force required to deflection the tip section 14. In the disclosed embodiment, a deviation angle θ may range between about 5 to 12 degrees, preferably between 6 and 10 degrees and more preferably between 7 and 8 degrees, when the lever arm is in the neutral position (namely, when α is at or near 0) (FIG. 11). Because the pulleys 72 each travel a circular path when translated by the lever arm 70, the angle θ can be further decreased by up to about 2-4 degrees (that is, down to about θ=3 degrees) during this translation (FIGS. 12, 13). In any case, given such a minimal range of the angle θ, most of the force that is applied to draw a puller wire proximally along the longitudinal axis 77 for deflecting the tip section in the direction of the off axis lumen in which that puller wire extends is advantageously met by the proximal translation of the pulley drawing that puller wire along the angle θ.

In accordance with the present invention, an initial neutral position (with little or no detectable deflection) (FIG. 11) in the tip section 14 can be readily calibrated by selective placement of the stops 76a, 76b distally or proximally along the divider 92. With the lever arm 70 resting in the neutral position, the operating position of each puller wire 32 is adjusted so that it is sufficiently taut in drawing the ends 109 of the springs 74 against the stops 76 without causing any detectable deflection in the tip section 14. In that regard, it is understood that the puller wires can also be adjusted to provide the catheter with a predetermined amount of free play so that the catheter body 12 and/or elements surrounding the puller wires (e.g., outer wall 20 and/or stiffening tube 22) can shrink or stretch, such as during sterilization of the catheter, without adversely deforming the puller wires. These adjustments of the stop position of each puller wire can also be made to compensate for certain characteristics in the catheter, including puller wires with unequal actual lengths and/or counterpart components in the steering assembly or the control handle that are not exact duplicates of each other in terms of size or operating characteristics.

In accordance with the present invention, each stop 76a, 76b is configured for coarse and fine adjustments of a stop location for each puller wire past which its proximal end (or its proximal end portion) cannot pass proximally. As described above in relation to FIGS. 11-13, the stop location of each stop 76a, 76b determines how much distance the corresponding pulley needs to be moved (or the corresponding puller wire needs to travel) proximally before the tip section 14 begins to deflect in that direction.

In enabling coarse (or incremental) adjustment in the stop position of each puller wire, each stop 76a, 76b is configured to adjustably engage with the divider 92 at a selected position along the longitudinal axis 77. In particular, an inner surface of each stop has a plurality of protrusions 136 that can engage with any of a series of recessions 138 formed on either side of the divider 92. As such, the position of each stop can be adjusted proximally or distally within the control handle along the axis 77, thereby adjusting proximally or distally the stop location.

In enabling fine adjustment, a set screw 140a, 140b is provided at the distal end 135a, 135b of each second channel 132a, 132b, where a distal end of each set screw can be moved proximally or distally by advancing or withdrawing the screws in the channels. A tunnel in the screw allows the puller wires to pass through and move distally or proximally through the screws, but the tunnel is sized to prevent the fasteners 111a, 111b, and/or the free end 109a, 109b of the springs 74a, 74b from moving proximally past the distal ends of the set screws. Accordingly, each set screw can be adjusted proximally or distally within the control handle relative to the axis 77, thereby enabling fine adjustment proximally or distally of the stop location for each puller wire.

Stop adjustments should be performed to attain a neutral position with little or no detectable deflection in the catheter tip section 14 before the housing halves 64, 66 are joined to each other. Significantly, the control handle 16 is configured such that it need not be fully assembled for the steering assembly 68 and deflection of the tip section 14 to be effectively tested and evaluated. In particular, the steering assembly 68 can be tested and evaluated when assembled within the housing half 66 and operated on by the deflection knob 88 mounted on the lever arm 70 without the housing half 64.

In other embodiments, one or more additional off axis lumens may be provided through which additional components, e.g., infusion tube, optic fiber, etc., may extend. Depending on the intended use of the catheter 10, it can further comprise additional features such as temperature sensing means, an optic fiber, an infusion tube, and/or an electromagnetic sensor. Additionally, smaller components, such as a temperature sensing means, could also extend through the second lumen in the tip section along with the puller wire and lead wire(s).

In the embodiments described above, the central lumen 18 of the catheter body 12 is used for passage of the electrode lead wires 30 as well as the two puller wires 32, compression coils 46 and, if present, thermocouple wires, electromagnetic sensor cable, optic fiber or infusion tube. It is understood that the catheter body 12 could alternatively comprise a plurality of lumens. However, the single central lumen 18 is preferred because it has been found that a single lumen body permits better control when rotating the catheter 10. The single central lumen 18 permits the puller wires 32, compression coils 46 and lead wires 30 to float freely within the catheter body 12. If such wires are restricted within multiple lumens, they tend to build up energy when the control handle 16 is rotated, resulting in the catheter body 12 having a tendency to rotate back if, for example, the handle 16 is released, or if bent around a curve, to flip over, either of which are undesirable performance characteristics.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A bi-directional catheter comprising:
    an elongated catheter body having proximal and distal ends;
    a catheter tip section at the distal end of the catheter body and having proximal and distal ends and first and second diametrically-opposed off-axis lumens;
    a tip electrode at the distal end of the catheter tip section;
    a control handle at the proximal end of the catheter body, the control handle having a longitudinal axis and comprising at least a steering assembly having a lever arm rotatable about an axis substantially perpendicular to the longitudinal axis, the steering assembly including at least two pulleys rotatably mounted on opposing portions of the lever arm;
    first and second puller wires, each puller wire having proximal and distal ends and extending from the control handle through the catheter body, wherein the first puller wire extends into the first lumen in the tip section and the second puller wire extends into the second lumen in the tip section, and wherein the distal end of each puller wire is anchored to the tip section; and
    a first stop member that defines a first stop position for the first puller wire and a second stop member that defines a second stop position for the second puller wire;
    wherein each puller wire is trained on a respective pulley and rotation of the lever arm results in proximal movement of one of said pulleys relative to the control handle thereby drawing proximally at least a segment of its respective puller wire for deflecting the tip section in the direction of the off-axis lumen in which that puller wire extends; and
    wherein each stop position is adjustable proximally and distally within the control handle.

2. A bi-directional catheter of claim 1, further comprising at least one ring electrode.

3. A bi-directional catheter of claim 1, wherein each of the puller wires is trained about its respective pulley for at least about 180 degrees.

4. A bi-directional catheter of claim 1, wherein each puller wire extends from the distal end of the control handle to its respective pulley at an angle of no greater than about 10 degrees from the longitudinal axis of the control handle.

5. A bi-directional catheter of claim 1, wherein each puller wire extends from the distal end of the control handle to its respective pulley at an angle ranging between about 7 and 10 degrees from the longitudinal axis of the control handle.

6. A bi-directional catheter of claim 1, wherein the control handle further comprises a deflection knob, wherein the deflection knob and the lever arm are rotationally coupled to each other.

7. A bidirectional catheter of claim 1, further comprising first and second constant force springs, each having a free end that is attached to a proximal end of a different puller wire.

8. A bi-directional catheter of claim 7, wherein the constant force springs are positioned distal of the pulleys.

9. A bi-directional catheter of claim 7, wherein the first and second stop members are positioned proximally of their respective springs.

10. A bi-directional catheter of claim 1, further comprising a divider extending along the longitudinal axis of the control handle, said divider directing the puller wires at a predetermined angle toward their respective pulleys.

11. A bi-directional catheter of claim 6, further comprising an adjustment knob configured to adjust tension of the deflection knob.

12. A bi-directional catheter of claim 10, wherein each stop is adjustably engaged with the divider.

13. A bi-directional catheter of claim 1, wherein each stop comprises means for finely adjusting the stop position.

14. A bi-direction catheter of claim 13, wherein the means for finely adjusting comprises a set screw.

15. A bi-directional catheter of claim 1, wherein each stop member is configured to guide at least a segment of its respective puller wire.

16. A bi-directional catheter comprising:
an elongated catheter body having proximal and distal ends;
a catheter tip section at the distal end of the catheter body and having proximal and distal ends and first and second diametrically-opposed off-axis lumens;
a tip electrode at the distal end of the catheter tip section;
a control handle at the proximal end of the catheter body, the control handle having a longitudinal axis and comprising at least a steering assembly having a lever arm rotatable about an axis substantially perpendicular to the longitudinal axis, the lever arm having two pulleys rotatably mounted thereon;
first and second puller wires, each puller wire having proximal and distal ends and extending from the control handle through the catheter body;
means for adjustably setting a stop position for each puller wire; and wherein the first puller wire extends into the first lumen in the tip section and the second puller wire extends into the second lumen in the tip section, and wherein the distal end of each puller wire is anchored to the tip section, and wherein a travel path of each puller wire within the control handle includes a turn away from the longitudinal axis of at least 180 degrees about a respective pulley; and
wherein rotation of the lever arm results in movement of one of said pulleys relative to the control handle thereby drawing at least a segment of its respective puller wire for deflecting the tip section in the direction of the off-axis lumen in which that puller wire extends.

17. A bi-directional catheter of claim 16, further comprising at least one ring electrode.

18. A bi-directional catheter of claim 16, wherein the proximal end of each puller wire is connected to a constant force spring.

19. A bi-directional catheter of claim 16, wherein a travel distance of a segment of a puller wire drawn by a pulley for deflection is about twice the travel distance of that pulley.

20. A bi-directional catheter of claim 16, wherein a segment of a puller wire drawn by a pulley for deflection extends at an angle of less than about 7 degrees from the longitudinal axis.

21. A bi-directional catheter of claim 16, wherein the means for adjustably setting the stop position comprises stop members, each of which releasably engages with an elongated member extending along the longitudinal axis of the control handle.

22. A bi-directional catheter of claim 21, wherein the general proximal end of each puller wire is prevented from moving proximally past its stop position.

23. A bi-directional catheter comprising:
an elongated catheter body having proximal and distal ends;
a catheter tip section at the distal end of the catheter body and having proximal and distal ends;
a tip electrode at the distal end of the catheter tip section;
a control handle at the proximal end of the catheter body, the control handle having a longitudinal axis and comprising at least a steering assembly having a lever arm rotatable about a throw axis, the steering assembly including at least two pulleys rotatably mounted on opposing portions of the lever arm;
first and second puller wires, each puller wire having proximal and distal ends and extending from the control handle through the catheter body; and
a first stop member that defines a first stop position for the first puller wire and a second stop member that defines a second stop position for the second puller wire;
wherein each puller wire is trained on a respective pulley and rotation of the lever arm results in proximal movement of one pulley and distal movement of the other pulley, the one pulley moved proximally drawing proximally at least a segment of its respective puller wire for deflecting the tip section.

24. A bidirectional catheter of claim 23, further comprising at least one ring electrode.

* * * * *

UNITED STATES PATENT AND TRADEMARK OFFICE
CERTIFICATE OF CORRECTION

| | | |
|---|---|---|
| PATENT NO. | : 8,021,327 B2 | Page 1 of 1 |
| APPLICATION NO. | : 12/355667 | |
| DATED | : September 20, 2011 | |
| INVENTOR(S) | : Thomas V. Selkee | |

It is certified that error appears in the above-identified patent and that said Letters Patent is hereby corrected as shown below:

On the Title Page

(57) Abstract, line 3.          After "U-turn"
                                 Insert -- around --

In the Claims

Column 13, Claim 7,             Delete
line 7.                          "bidirectional"
                                 Insert
                                 -- bi-directional --

Column 14, Claim 24,            Delete
line 50.                         "bidirectional"
                                 Insert
                                 -- bi-directional --

Signed and Sealed this
Eighth Day of May, 2012

David J. Kappos
*Director of the United States Patent and Trademark Office*